United States Patent [19]

Takaya et al.

[11] Patent Number: 4,504,472
[45] Date of Patent: Mar. 12, 1985

[54] 1,4-DIAMINOCYCLITOL DERIVATIVES

[75] Inventors: Takao Takaya, Kawanishi; Hideo Tsutsumi, Toyonaka; Nobuyuki Yasuda, Nishinomiya; Keiji Matsuda, Takatsuki, all of Japan

[73] Assignee: Fujisawa Pharmaceutical Co., Ltd., Osaka, Japan

[21] Appl. No.: 470,449

[22] Filed: Feb. 28, 1983

[30] Foreign Application Priority Data

Mar. 5, 1982 [GB] United Kingdom ................ 8206609

[51] Int. Cl.$^3$ ...................... A61K 31/71; C07H 15/22
[52] U.S. Cl. .................................... 514/36; 536/16.1; 536/16.8
[58] Field of Search ............... 424/180; 536/16.1, 16.8

[56] References Cited

U.S. PATENT DOCUMENTS

| | | | |
|---|---|---|---|
| 4,155,902 | 5/1979 | Tadanier et al. | 260/112.5 R |
| 4,187,297 | 2/1980 | Martin et al. | 424/180 |
| 4,226,980 | 10/1980 | Sato et al. | 536/16.1 |
| 4,251,516 | 6/1981 | Martin et al. | 424/180 |
| 4,255,421 | 3/1981 | Watanabe et al. | 424/180 |
| 4,276,413 | 6/1981 | Martin et al. | 536/16.1 |
| 4,360,666 | 11/1982 | Tadanier et al. | 536/16.1 |

FOREIGN PATENT DOCUMENTS 2742950 3/1978 Fed. Rep. of Germany ..... 536/16.1

OTHER PUBLICATIONS

The Journal of Antibiotics, vol. 34, No. 7, Jul. 1981, Tokyo (JP) T. Deushi et al.: "A New Broad-Spectrum Aminoglycoside Antibiotic Complex, Sporaricin", pp. 811–817.

Primary Examiner—Johnnie R. Brown
Attorney, Agent, or Firm—Oblon, Fisher, Spivak, McClelland & Maier

[57] ABSTRACT

This invention relates to novel, 1,4-diaminocyclitol derivatives of antimicrobial and immunostimulating activity of the formula:

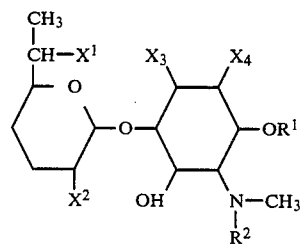

wherein $X^1$, $X^2$ and $X^3$ are each amino or protected amino,
$X^4$ is hydrogen or hydroxy,
$R^1$ is hydrogen or lower alkyl, and
$R^2$ is higher alkanoyl permissably substituted with hydroxy, amino, azido, epoxy, protected hydroxy or protected amino, or higher alkenoyl, or higher alkylcarbanoyl,
and pharmaceutically acceptable salts thereof.

18 Claims, No Drawings

1,4-DIAMINOCYCLITOL DERIVATIVES

This invention relates to new 1,4-diaminocyclitol derivatives and pharmaceutically acceptable salts thereof. More particularly, it relates to new 1,4-diaminocyclitol derivatives and pharmaceutically acceptable salts thereof which have antimicrobial activity (e.g. antibacterial activity, antiviral activity, etc.) and immuno-stimulating activity, processes for the preparation thereof and a pharmaceutical composition comprising the same.

Accordingly, it is an object of this invention to provide new 1,4-diaminocyclitol derivatives which are useful as prophylactic and therapeutic agents for infectious diseases caused by pathogenic microorganisms.

Another object of this invention is to provide processes for preparing the 1,4-diaminocyclitol derivatives.

Further object of this invention is to provide a pharmaceutical composition comprising the 1,4-diaminocyclitol derivatives.

The object new 1,4-diaminocyclitol derivatives of this invention can be represented by the following formula:

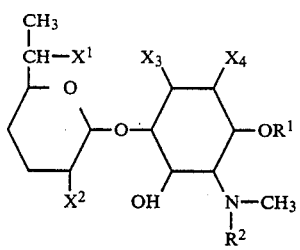

wherein
  $X^1$, $X^2$ and $X^3$ are each amino or protected amino,
  $X^4$ is hydrogen or hydroxy,
  $R^1$ is hydrogen or lower alkyl, and
  $R^2$ is higher alkanoyl which may have one or more suitable substituent(s), higher alkenoyl, or higher alkylcarbamoyl,
and pharmaceutically acceptable salts thereof.

According to this invention, the new 1,4-diaminocyclitol derivatives (I) and pharmaceutically acceptable salts thereof can be prepared by, for example, the following processes.

Process 1:

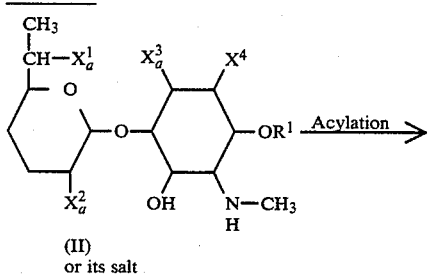

Process 2:

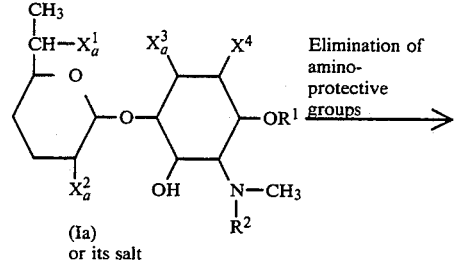

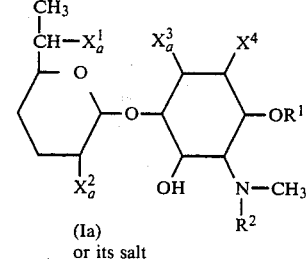
(Ia)
or its salt

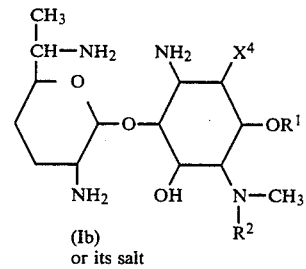
(Ib)
or its salt

Process 3:

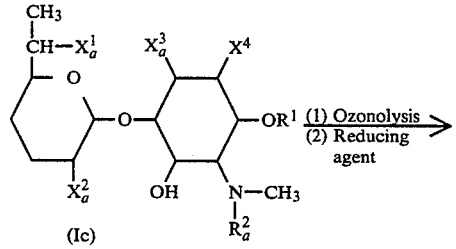

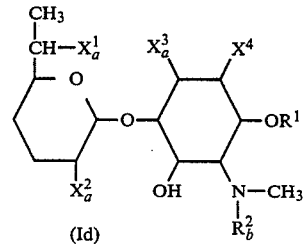
(Id)

Process 4:

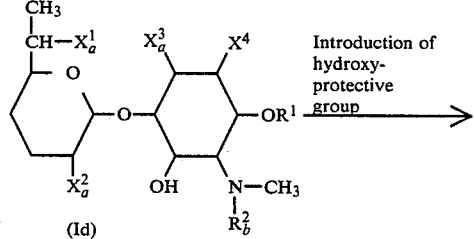

-continued

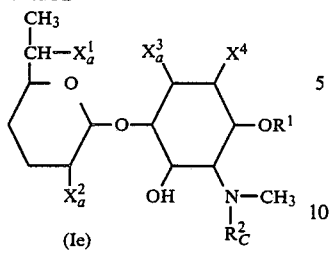
(Ie)

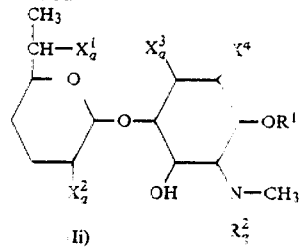
(Ii)

Process 5:

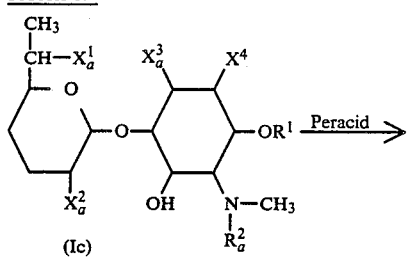
(Ic)

Peracid →

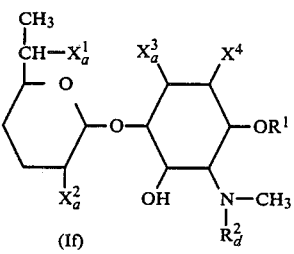
(If)

Process 6:

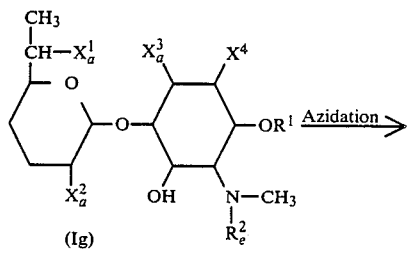
(Ig)

Azidation →

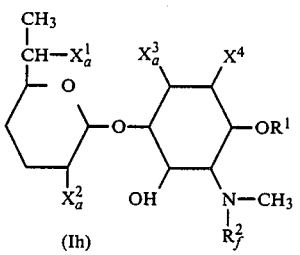
(Ih)

Process 7:

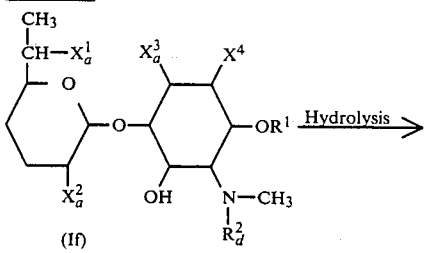
(If)

Hydrolysis → wherein
$X^4$, $R^1$ and $R^2$ are each as defined above,
$X_a^1$, $X_a^2$ and $X_a^3$ are each protected amino,
$R_a^2$ is higher alkenoyl,
$R_b^2$ is higher alkanoyl having hydroxy,
$R_c^2$ is higher alkanoyl having a protected hydroxy,
$R_d^2$ is higher alkanoyl having epoxy,
$R_e^2$ is higher alkanoyl having epoxy or protected hydroxy,
$R_f^2$ is higher alkanoyl having azido or azido and hydroxy, and
$R_g^2$ is higher alkanoyl having two hydroxy groups.

The starting compound (II) or its salt can be prepared by introducing the corresponding amino-protective group into the known compounds, for example, sporaricin B (code name: KA-6606 II) or 5-de-O-methyl-sporaricin B (code name: de-O-methyl-KA-6606 II) or their salts. [cf. THE JOURNAL OF ANTIBIOTICS VOL. XXXII, Page 187 (1979) and U.S. Pat. No. 4,255,421]; or fortimicin B, 3-de-O-methylfortimicin B, 2-deoxy-3-de-O-methylfortimicin B (cf. U.S. Pat. Nos. 4,155,902, 4,187,297 and 4,251,516).

Suitable pharmaceutically acceptable salts of 1,4-diominocyclitol derivatives (I) and conventional non-toxic salt and may include an organic or inorganic acid addition salt such as hydrochloride, hydrobromide, hydriodide, sulfate, nitrate, carbonate, phosphate, acetate, fumarate, maleate, tartrate, methanesulfonate, benzenesulfonate, toluenesulfonate, and the like. In the above and subsequent descriptions of this specification, suitable examples and illustrations of the various definitions are explained in detail in the followings.

The term "lower" is intended to mean 1 to 6 carbon atom(s).

The term "higher" used in the specification is intended to mean more than 7 carbon atoms, preferably 8 to 24 carbon atoms.

"Protected amino" means an amino group protected by a conventional amino-protective group such as an acyl, for example, lower alkoxycarbonyl (e.g. methoxycarbonyl, ethoxycarbonyl, propoxycarbonyl, isopropoxycarbonyl, butoxycarbonyl, isobutoxycarbonyl, t-butoxycarbonyl, pentyloxycarbonyl, etc.), ar(lower)alkoxycarbonyl which may have nitro or lower alkoxy (e.g. benzyloxycarbonyl, p-nitrobenzyloxycarbonyl, p-methoxybenzyloxycarbonyl, etc.), lower alkanoyl (e.g. formyl, acetyl, etc.), higher alkanoyl (e.g. the same as exemplified below, etc.), ar(lower)alkylidene (e.g. salicylidene, etc.), ar(lower)alkyl which may have nitro (e.g. benzyl, p-nitrobenzyl, benzhydryl, trityl, etc.), lower alkylsulfonyl (e.g. methanesulfonyl, etc.), ar(lower)alkylsulfonyl (e.g. benzylsulfonyl, etc.), arenesulfonyl (e.g. toluenesulfonyl, etc.), or the like.

"Lower alkyl" may include methyl, ethyl, propyl, isopropyl, butyl, isobutyl, t-butyl and the like.

"Higher alkanoyl which may have one or more suitable substituent(s)" means higher alkanoyl (e.g. octanoyl, lauroyl, myristoyl, palmitoyl, stearoyl, eicosanoyl, docosanoyl, tetracosanoyl, etc.) which may have one or more suitable substituent(s) such as hydroxy, amino, azido, epoxy, protected hydroxy, protected amino and the like.

"Protected hydroxy" means a hydroxy group protected by a conventional hydroxy-protective group such as those as exemplified as amino-protective group.

"Higher alkenoyl" may include octenoyl, undecenoyl, oleoyl and the like.

"Higher alkylcarbamoyl" may include octylcarbamoyl, nonylcarbamoyl, decanylcarbamoyl, undecanylcarbamoyl, dodecanylcarbamoyl, tridecanylcarbamoyl, tetradecanylcarbamoyl, pentadecanylcarbamoyl, hexadecanylcarbamoyl, heptadecanylcarbamoyl, octadecanylcarbamoyl, nonadecanylcarbamoyl, eicosanylcarbamoyl, heneicosanylcarbamoyl, docosanylcarbamoyl, tricosanylcarbamoyl, tetracosanylcarbamoyl, and the like.

The processes for preparing the object compounds of this invention are explained in details in the following.

PROCESS 1

The object compound (Ia) or its salt can be prepared by reacting the compound (II) or its salt with an acylating agent for introducing an acyl group of the formula: —$R^2$ (wherein $R^2$ is as defined above).

Suitable said acylating agent may include a compound of the formula: $R^2$—OH (wherein $R^2$ is as defined above) or its reactive derivative, for example, acid halide (e.g. acid chloride, acid bromide, etc.), acid anhydride, acid azido, activated amide or activated ester (e.g. succinimide ester, p-nitrophenyl ester, etc.), or the corresponding higher alkyl isocyanate (e.g. pentadecanyl isocyanate, etc.).

The reaction can preferably be conducted in the presence of an organic or inorganic base such as alkali metal (e.g. sodium), alkaline earth metal (e.g. calcium), alkali or alkaline earth metal hydride (e.g. sodium hydride, calcium hydride, etc.), alkali or alkaline earth metal hydroxide (e.g. sodium hydroxide, potassium hydroxide, calcium hydroxide, etc.), alkali or alkaline earth metal carbonate or bicarbonate (e.g. sodium carbonate, potassium carbonate, sodium bicarbonate), alkali or alkaline earth metal alkoxide (e.g. sodium ethoxide, lithium methoxide, magnesium methoxide), trialkylamine (e.g. triethylamine), pyridine, bicyclodiaza compound (e.g. 1,5-diazabicyclo[3,4,0]nonene-5, 1,5-diazabicyclo[5,4,0]undecene-5, etc.) and the like.

When the acylating agent is used in a form of free acid, the reaction of this process may preferably be conducted in the presence of a condensing agent such as carbodiimidic compound (e.g. N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.), N,N'-carbonyldiimidazole, N,N'-carbonyldi(2-methylimidazole), pentamethyleneketene-N-cyclohexylimine, diphenylketene-N-cyclohexylimine, alkoxyacetylene, 1-alkoxy-1-chloroethylene, trialkylphosphite, ethyl polyphosphate, isopropyl polyphosphate, phosphorus compound (e.g. phosphorus oxychloride, phosphorus trichloride, etc.), thionyl chloride, oxalyl chloride, 2-ethyl-7-hydroxybenzisoxazolium salt, 2,2,4,4,6,6-hexachloro 1,3,5,2,4,6-triazatriphosphorine, 1-benzenesulphonyloxy-6-chloro-1H-benzotriazole, p-toluenesulfonyl chloride, isopropoxybenzenesulfoxyl chloride, or a mixed condensing agent such as triphenylphosphine and a carbon tetrahalide (e.g. carbon tetrachloride, carbon tetrabromide, etc.) or so-called Vilsmeier reagent (e.g. a complex of N,N-dimethylformamide with phosphoryl chloride, phosgene or thionyl chloride, etc.), and the like.

The reaction is usually conducted in a conventional solvent which does not adversely influence the reaction such as water, acetone, dioxane, acetonitrile, ethyl acetate, N,N-dimethylformamide, dimethylsulfoxide, tetrahydrofuran, dichloromethane, chloroform, pyridine, N-methylmorpholine, N-methylpyrrolidine, etc. or a mixture thereof.

The reaction temperature is not critical and this reaction can be conducted within the temperature range of cooling to heating.

PROCESS 2

The object compound (Ib) or its salt can be prepared by subjecting the compound (Ia) or its salt to an elimination reaction of the amino-protective groups.

This elimination reaction can be carried out in conventional manners such as hydrolysis, reduction in combination of hydrolysis and reduction, and the like.

The reduction may include chemical reduction and catalytic reduction. Suitable examples of the catalyst for the catalytic reduction may include platinum catalyst such as platinum plate, spongy platinum, platinum black, platinum colloid, platinum oxide or platinum wire; palladium catalyst such as palladium spongy, palladium black, palladium oxide, palladium on charcoal or palladium colloid; platinum group metal catalyst such as iridium, iridium colloid, luthenium oxide, rhodium colloid or rhodium on alumina, nickel catalyst such as reduced nickel, nickel oxide or Raney nickel; cobalt catalyst such as reduced cobalt or Raney cobalt; iron catalyst such as reduced iron or Raney iron; or copper catalyst such as reduced copper, Raney copper or Ullmann copper.

This catalytic reduction can usually be carried out under atmospheric or increasing pressures of hydrogen.

The hydrolysis is carried out in the presence of an acid (e.g. trifluoroacetic acid, etc.) or a base (e.g. potassium hydroxide, etc.).

In case that the starting compound (Ia) wherein $R^2$ is higher alkanoyl having an azido group is subjected to reduction in this process there is occasionally produced the object compound (Ib) wherein $R^2$ is higher alkanoyl having an amino group.

This reaction is usually carried out without a solvent or in a conventional solvent which does not adversely influence the reaction such as water, methanol, ethanol, propanol, tetrahydrofuran, N,N-dimethylformamide, dioxane, dichloromethane, acetic acid, hydrochloric acid and a mixture thereof.

The reaction temperature of the elimination is not critical and the reaction can be carried out from under cooling to under warming. In case that the starting compound (Ia) possesses protected amino group(s) and/or protected hydroxy group(s), these protected group(s) are occasionally converted to the corresponding free amino group(s) and/or hydroxy group(s) during this reaction.

PROCESS 3

The object compound (Id) can be prepared by reacting the compound (Ic) with ozone and then reacting the resultant compound with a reducing agent.

The reducing agent may include alkali metal borohydride [e.g. sodium borohydride, etc.] and the like.

This reaction is usually conducted in a conventional solvent which does not adversely influence the reaction such as dichloromethane, chloroform, methanol, ethanol, etc. or a mixture thereof.

This reaction is usually carried out under cooling.

PROCESS 4

The compound (Ie) can be prepared by subjecting the compound (Id) to introduction reaction of hydroxyprotective group.

This reaction is usually carried out by using an introducing agent of a hydroxy protective group such as an acylating agent, for example, alkanesulfonyl halide (e.g. mesyl chloride, etc.), arenesulfonyl halide (e.g. p-toluenesulfonyl chloride, etc.), and the like.

This reaction can be carried out in the presence of an inorganic or organic base.

This reaction is usually carried out in the presence of a conventional solvent which does not adversely influence this reaction such as ethyl ether, tetrahydrofuran, ethyl acetate, dimethylsulfoxide, chloroform, pyridine and the like.

This reaction temperature is not critical and the reaction can be carried out under cooling to heating.

PROCESS 5

The compound (If) can be prepared by reacting the compound (Ic) with a peracid.

Preferred examples of a peracid may include aryl percarboxylic acid (e.g. perbenzoic acid, m-chloroperbenzoic acid, etc.) and the like.

The reaction is conducted in a conventional solvent which does not adversely influence this reaction such as methanol, ethanol, chloroform, methylenechloride and the like under cooling to heating.

PROCESS 6

The compound (Ih) can be prepared by reacting the compound (Ig) with an azidating agent.

The azidating agent may include alkali metal azide (e.g. sodium azide, etc.), ammonium azide and the like.

This reaction is usually carried out in the presence of a conventional solvent which does not adversely influence this reaction such as N,N-dimethylformamide, dimethylsulfoxide, hexamethylphosphoric triamide, methanol, ethanol, a mixture thereof and the like within a temperature range of ambient temperature to heating.

PROCESS 7

The compound (Ii) can be prepared by hydrolyzing the compound (If).

This hydrolysis is preferably carried out in the presence of an inorganic or organic acid (e.g. trifluoroacetic acid, hydrochloric acid, etc.).

The reaction is usually carried out in the absence or presence of a conventional solvent which does not adversely influence such as water, methanol, ethanol and the like.

This reaction temperature is not critical and this reaction can be conducted within the temperature range of cooling to heating.

The object compounds (Ia), (Ib), (Id), (Ie), (If), (Ih) and (Ii) can be isolated, purified and converted to the desired salts in a conventional manner.

The object compound (I) and pharmaceutically acceptable salts thereof possesses an antimicrobial activity (e.g. antibacterial acivity, antiviral activity against virus such as herpes virus I, II, influenza virus and the like, etc.) and immuno-stimulating activity and therefore, are useful as an antimicrobial agent (e.g. antibacterial agent, antiviral agent, etc.) for human beings, animals and plants and a prophylactic agent for infectious diseases caused by pathogenic microorganisms.

For prophylactic or therapeutic administration, the object compound (I) and the pharmaceutically acceptable salts thereof of the present invention are used in the form of conventional pharmaceutical preparation comprising the same, as active ingredients, in admixture comprising the same, as active ingredients, in admixture with pharmaceutically acceptable carriers such as an organic or inorganic solid or liquid excipient which is suitable for oral, parenteral and external administration. The pharmaceutical preparations may be in solid form such as tablet, granule, powder, capsule, or liquid form such as solution, suspension, syrup, emulsion, lemonade, or semisolid form such as ointment and the like.

If needed, there may be included in the above preparations auxiliary substances, stabilizing agents, wetting agents and other commonly used additives such as lactose, magnesium stearate, terra alba, sucrose, corn starch, talc, stearic acid, gelatin, agar, pectin, peanut oil, olive oil, cacao butter, polyethylene glycol, mineral oil, white bees wax, white petrolatum and the like.

While the dosage of the compound (I) or pharmaceutically acceptable salts thereof may vary from and also depend upon the age, conditions of the patient, a kind of diseases, a kind of the compound (I) or pharmaceutically acceptable salts thereof to be applied, etc. In general, preferable dosage of the compound (I) or pharmaceutically acceptable salts thereof to the patient can be selected from 0.1–100 mg/kg/day.

The following Examples are given for the purpose of illustrating this invention. In the Examples, it is to be noted that numbering of carbon atom's position of sporaricin B or fortimicin B derivatives is given in accordance with those of sporaricin B or fortimicin B as illustrated as follows, respectively.

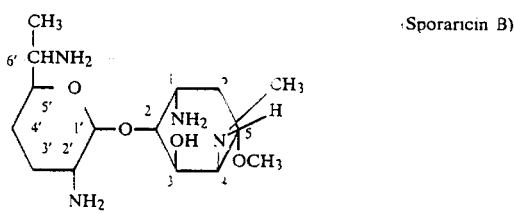

Sporaricin B

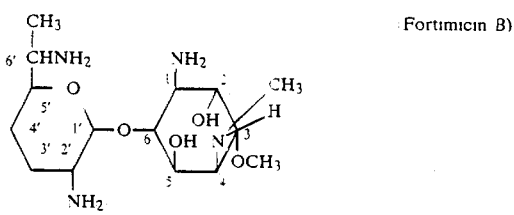

Fortimicin B

EXAMPLE 1

(1) To a solution of 1,2',6'-tris-N-benzyloxycarbonyl-5-de-O-methylsporaricin B in a mixture of tetrahydrofuran (20 ml) and water (5 ml), was dropwise added palmitoyl chloride (458 mg) at 0°–10° C. with stirring, keeping the pH between 8 and 10 with triethylamine. The reaction mixture was stirred at the same temperature for 30 minutes. Tetrahydrofuran was removed from the reaction mixture by evaporation in vacuo. The residue was extracted with ethyl acetate. The extract was washed twice with saturated aqueous sodium chloride, dried over magnesium sulfate, and concentrated under reduced pressure. The residue was purified by column chromatography on silica gel [chloroform-methanol (100:1 V/V], to give 1,2',6'-tris-N-benzyloxycarbonyl-4-N-palmitoyl-5-de-O-methylsporaricin B.

NMR (CDCl$_3$, $\delta$): 3.00 (3H, s).

(2) A solution of 1,2',6'-tris-N-benzyloxycarbonyl-4-N-palmitoyl-5-de-O-methylsporaricin B (680 mg) in a mixture of methanol (15 ml) and conc. hydrochloric acid (1.5 ml) was hydrogenated under hydrogen atmosphere (1 atm) at ambient temperature for 3 hours in the presence of 10% palladium on carbon (400 mg). The catalyst was filtered off. The filtrate was concentrated under reduced pressure. To the residue was added aqueous ethanol and the mixture was concentrated under reduced pressure to give a residue, which was lyophilized to give 4-N-palmitoyl-5-de-O-methylsporaricin B trihydrochloride (363 mg).

mp; 236° C. (dec.).
$[\alpha]_D^{20}$; +81.1° (C 1.0, H$_2$O).
IR (Nujol); 1600 cm$^{-1}$.
NMR (D$_2$O, $\delta$): 3.13 (3H, s,), 5.50 (1H, d, J=3 Hz).
FD Mass; 557 (M+).

EXAMPLE 2

(1) The following compound was obtained according to a similar manner to Example 1 (1). 1,2',6'-Tris-N-benzyloxycarbonyl-4-N-octanoyl-5-de-O-methylsporaricin B.

NMR (CDCl$_3$, $\delta$); 3.00 (3H, s)

(2) The following compound was obtained according to a similar manner to that of Example 1 (2). 4-N-Octanoyl-5-de-O-methylsporaricin B trihydrochloride.

mp; 233° C. (dec.).
$[\alpha]_D^{20}$; +102.7° (C 1.0, H$_2$O).
IR (Nujol); 1600 cm$^{-1}$.
NMR (D$_2$O, $\delta$); 3.17 (3H, s), 5.53 (1H, d, J=3 Hz).
FD Mass; 445 (M+).

EXAMPLE 3

(1) The following compound was obtained according to a similar manner to that of Example 1 (1). 1,2',6'-Tris-N-benzyloxycarbonyl-4-N-decanoyl-5-de-O-methylsporaricin B.

NMR (CDCl$_3$, $\delta$); 3.00 (3H, s).

(2) The following compound was obtained according to a similar manner to that of Example 1 (2). 4-N-Decanoyl-5-de-O-methylsporaricin B trihydrochloride.

mp; 231° C. (dec.).
IR (Nujol); 1600 cm$^{-1}$.
NMR (D$_2$O, $\delta$); 3.17 (3H, s), 5.53 (1H, d, J=3 Hz).
FD Mass; 473 (M+).

EXAMPLE 4

(1) The following compound was obtained according to a similar manner to that of Example 1 (1). 1,2',6'-Tris-N-benzyloxycarbonyl-4-N-lauroyl-5-de-O-methylsporaricin B.

NMR (CDCl$_3$, $\delta$); 3.00 (3H, s).

(2) The following compound was obtained according to a similar manner to that of Example 1 (2). 4-N-Lauroyl-5-de-O-methylsporaricin B trihydrochloride.

mp; 229° C. (dec.);
$[\alpha]_D^{20}$; +107.2° (C 1.0, H$_2$O);
IR (Nujol); 1600 cm$^{-1}$;
NMR (D$_2$O, $\delta$); 3.13 (3H, s), 5.50 (1H, d, J=3 Hz);
FD Mass; 501 (M+).

EXAMPLE 5

(1) The following compound was obtained according to a similar manner to that of Example 1 (1). 1,2',6'-Tris-N-benzyloxycarbonyl-4-N-myristoyl-5-de-O-methylsporaricin B.

NMR; 3.00 (3H, s).

(2) The following compound was obtained according to a similar manner to that of Example 1 (2). 4-N-Myristoyl-5-de-O-methylsporaricin B trihydrochloride.

mp; 222° C. (dec.);
$[\alpha]_D^{20}$; +101.6° (C 1.0, H$_2$O);
IR (Nujol); 1600 cm$^{-1}$;
NMR (D$_2$O, $\delta$); 3.13 (3H, s), 5.50 (1H, d, J=3 Hz);
FD Mass; 529 (M+).

EXAMPLE 6

(1) The following compound was obtained according to a similar manner to that of Example 1 (1). 1,2',6'-Tris-N-benzyloxycarbonyl-4-N-stearoyl-5-de-O-methylsporaricin B.

IR (Nujol); 1690, 1610, 1510 cm$^{-1}$.
NMR (CDCl$_3$ $\delta$); 3.00 (3H, s).

(2) The following compound was obtained according to a similar manner to that of Example 1 (2). 4-N-Stearoyl-5-de-O-methylsporaricin B trihydrochloride.

mp; 228° C. (dec.).
$[\alpha]_D^{20}$; +72.2° (C 1.0, H$_2$O).
IR (Nujol); 1600 cm$^{-1}$.
NMR (CDCl$_3$, $\delta$); 3.13 (3H, s), 5.47 (1H, d, J=3 Hz).
FD Mass; 585 (M+).

EXAMPLE 7

(1) Phosphorus oxychloride (0.22 ml) was added to a mixture of N,N-dimethylformamide (0.18 ml) and tetrahydrofuran (0.3 ml) at 5°–8° C. and stirred at −15° C. until colorless precipitates were appeared. Tetrahydrofuran (6 ml) was added to the resultant mixture. The reaction mixture was stirred at 0°–5° C. for 10 minutes. Eicosanoic acid (563 mg) was added to the mixture at 0°–5° C. and the solution was stirred at the same temperature for 1 hour. On the other hand, 1,2',6'-tris-N-benzyloxycarbonyl-5-de-O-methylsporaricin B (1 g) was dissolved in a mixture of tetrahydrofuran (20 ml) and water (5 ml). To the solution was dropwise added the above activated acid solution at 0°–10° C. with stirring, keeping the pH between 8 and 10 with triethylamine. The reaction mixture was stirred at the same temperature for 30 minutes. Tetrahydrofuran was removed from the reaction mixture by evaporation in vacuo. The residue was extracted with ethyl acetate. The extract was washed twice with saturated aqueous sodium chloride, dried over magnesium sulfate, and concentrated under reduced pressure. The residue was purified by a column chromatography on silica gel [chloroform-methanol (100:1 V/V)] to give 1,2',6'-tris-N-benzyloxycarbonyl-4-N-eicosanoyl-5-de-O-methylsporaricin B (1.08 g).

NMR (CDCl$_3$, δ); 3.00 (3H, s).

(2) The following compound was obtained according to a similar manner to that of Example 1 (2). 4-N-Eicosanoyl-5-de-O-methylsporaricin B trihydrochloride.

mp; 235° C. (dec.).

[α]$_D^{20}$; +82.7° (C 1.0, H$_2$O).

IR (Nujol); 1600 cm$^{-1}$.

NMR (D$_2$O, δ); 3.13 (3H, s), 5.53 (1H, d, J=3 Hz).

FD Mass; 613 (M+).

EXAMPLE 8

(1) Phosphorus oxychloride (0.33 ml) was added to a mixture of N,N-dimethylformamide (0.28 ml) and tetrahydrofuran (0.5 ml) at 5°-8° C. and stirred at −15° C. until colorless precipitates were applied. N,N-Dimethylformamide (5 ml) was added to the resultant mixture, to which a hot solution of docosanoic acid (945 mg) in N,N-dimethylformamide (5 ml) was added. The mixture was stirred at ambient temperature for 30 minutes and then at 40° C. for 30 minutes. To a solution of 1,2′,6′-tris-N-benzyloxycarbonyl-5-de-O-methylsporaricin B (1 g) in a mixture of tetrahydrofuran (20 ml) and water (5 ml) was dropwise added the activated acid solution under ice-cooling with stirring, keeping the pH between 8 and 10 with triethylamine. The reaction mixture was stirred under ice-cooling for 30 minutes. Tetrahydrofuran was removed from the reaction mixture by evaporation in vacuo. The residue was dissolved in ethyl acetate. The ethyl acetate solution was washed with saturated aqueous sodium chloride, dried over magnesium sulfate, and concentrated under reduced pressure. The residue was purified by a column chromatography on silica gel to give 1,2′,6′-tris-N-benzyloxycarbonyl-4-N-docosanoyl-5-de-O-methylsporaricin B (1.09 g).

(2) The following compound was obtained according to a similar manner to that of Example 1 (2). 4-N-Docosanoyl-5-de-O-methylsporaricin B trihydrochloride.

mp; 215° C. (dec.).

[α]$_D^{21}$; +79.1° (C 1.0, H$_2$O).

IR (Nujol); 1600, 1500 cm$^{-1}$.

NMR (D$_2$O, δ); 3.14 (3H, s), 5.53 (1H, d, J=3 Hz).

FD Mass; 641 (M+).

EXAMPLE 9

(1) To a solution of 1,2′,6′-tris-N-benzyloxycarbonyl-5-de-O-methylsporaricin B (721 mg) in dry tetrahydrofuran (100 ml) was added under ice-cooling (3RS)-3-hydroxytetradecanoyloxysuccinimide (410 mg) and the mixture was stirred overnight at ambient temperature. The reaction mixture was concentrated in vacuo to give the residue. The residue was purified by a column chromatography on silica gel (30 g) [chloroform-methanol 40:1 (V/V)] to give 1,2′,6′-tris-N-benzyloxycarbonyl-4-N-[(3RS)-3-hydroxytetradecanoyl]-5-de-O-methylsporaricin B (269 mg).

NMR (CDCl$_3$, δ); 3.00 (3H, s).

FD Mass; 947 (M+).

(2) The following compound was obtained according to a similar manner to that of Example 1 (2). 4-N-[(3RS)-3-Hydroxytetradecanoyl]-5-de-O-methylsporaricin B trihydrochloride.

mp; 235° C. (dec.).

[α]$_D^{20}$; +84.8° (C 0.25, H$_2$O).

IR (Nujol); 1600 cm$^{-1}$.

NMR (CDCl$_3$, δ); 3.13 (3H, s), 5.47 (1H, d, J=3 Hz).

EXAMPLE 10

(1) To a solution of t-butyl (3RS)-3-hydroxytetradecanoate (20.0 g) in dry pyridine (100 ml) was added acetic anhydride (7.8 ml) at ambient temperature. The mixture was stirred at the same temperature overnight. Acetic anhydride (3 ml) was added to the mixture. The mixture was stirred for additional 2 hours at the same temperature. To the mixture was added methanol (50 ml) under ice-cooling. The mixture was concentrated under reduced pressure. The residue was dissolved in ethyl acetate. The organic solution was washed with 1N hydrochloric acid and saturated aqueous sodium chloride, dried over magnesium sulfate, and concentrated under reduced pressure. The residue was purified by a column chromatography on silica gel (400 g) (chloroform:methanol 100:1 V/V) to give t-butyl (3RS)-3-acetoxytetradecanoate (14.04 g).

IR (neat); 2920, 2850, 1730, 1460, 1360, 1230, 1150, 1020 cm$^{-1}$.

NMR (CCl$_4$, δ); 1.40 (9H, s), 1.97 (3H, s), 2.37 (2H, d, J=7 Hz), 5.07 (1H, m).

(2) Trifluoroacetic acid (32 ml) was added to t-butyl (3RS)-3-acetoxytetradecanoate (14 g) under ice-cooling. The mixture was stirred at the same temperature for 2 hours. The mixture was concentrated under reduced pressure to give a residue. The residue was dissolved in a mixture of benzene and toluene, and concentrated under reduced pressure to give (3RS)-3-acetoxytetradecanoic acid (10.0 g).

mp; 37° C.

IR (Nujol); 1730, 1710, 1230 cm$^{-1}$.

(3) The following compound was obtained according to a similar manner to that of Example 7 (1). 4-N-[(3RS)-3-Acetoxytetradecanoyl]-1,2′,6′-tris-N-benzyloxycarbonyl-5-de-O-methylsporaricin B.

(4) To a solution of 4-N-[(3RS)-3-acetoxytetradecanoyl]-1,2′,6′-tris-N-benzyloxycarbonyl-5-de-O-methylsporaricin B (10.76 g) in methanol (200 ml) was added potassium hydroxide (1.22 g) at ambient temperature. The mixture was stirred for 3 hours at the same temperature. Acetic acid (1.9 ml) was added to the mixture and the mixture was concentrated in vacuo. The residue was dissolved in ethyl acetate. The ethyl acetate solution was washed with aqueous potassium carbonate and saturated aqueous sodium chloride, dried over magnesium sulfate, and concentrated in vacuo. The residue (9.5 g) was separated by a column chromatography on silica gel (400 g) (chloroform:ethanol=100:1 V/V, and then chloroform:ethanol=50:1 V/V) to give fractions (first Fraction A and second Fraction B). From the first Fraction A, one diastereomer of 1,2′,6′-tris-N-benzyloxycarbonyl-4-N-(3-hydroxytetradecanoyl)-5-de-O-methylsporaricin B (Diastereomer A) (2.46 g) was obtained.

[α]$_D^{21}$; +27.0° (C 1.0, CHCl$_3$).

IR (CHCl$_3$); 1700, 1610 cm$^{-1}$.

NMR (CDCl$_3$, δ); 3.03 (3H, s).

Further, from the second Fraction B, another diastereomer of 1,2′,6′-tris-N-benzyloxycarbonyl-4-N-(3-hydroxytetradecanoyl)-5-de-O-methylsporaricin B (Diastereomer B) (3.21 g) was obtained.

[α]$_D^{21}$; +65.4° (C 1.0, CHCl$_3$).

IR (CHCl$_3$); 1700, 1610 cm$^{-1}$.

NMR (CDCl$_3$, δ); 3.03 (3H, s).

(5) The following compound was obtained according to a similar manner to that of Example 1 (2). One diastereomer of 4-N-(3-hydroxytetradecanoyl)-5-de-O- methylsporaricin B trihydrochloride from the Diastereomer B obtained above (4).

mp; 215° C. (dec.).
$[\alpha]_D^{21}$; +90.5° (C 1.0, H$_2$O).
IR (Nujol); 1600, 1500 cm$^{-1}$.
NMR (D$_2$O, δ); 3.17 (3H, s), 5.53 (1H, d, J=3 Hz).
FD Mass; 545 (M+).

(6) The following compound was obtained according to a similar manner to that of Example 1 (2). Another diastereomer of 4-N-(3-hydroxytetradecanoyl)-5-de-O-methylsporaricin B trihydrochloride from the Diastereomer A obtained above (4).

mp; 226° C. (dec.).
$[\alpha]_D^{21}$; +77.1° (C 1.0, H$_2$O).
IR (Nujol); 1600, 1500 cm$^{-1}$.
NMR (D$_2$O, δ); 3.17 (3H, s), 5.53 (1H, d, J=3 Hz).
FD Mass; 545 (M+).

EXAMPLE 11

(1) The following compound was obtained according to a similar manner to that of Example 1 (1). 1,2',6'-Tris-N-t-butoxycarbonyl-4-N-oleoyl-5-de-O-methylsporaricin B.

IR (Nujol); 1710–1680, 1620 cm$^{-1}$.
NMR (CDCl$_3$, δ); 3.17 (3H, s).

(2) A solution of 1,2',6'-tris-N-t-butoxycarbonyl-4-N-oleoyl-5-de-O-methylsporaricin B (438 mg) in a mixture of anisole (2.5 ml) and trifluoroacetic acid (10 ml) was stirred for 2 hours under ice-cooling. The resultant mixture was concentrated under reduced pressure. To the residue was added toluene and ethanol. The mixture was concentrated in vacuo. The residue was purified by a column chromatography using Amberlite IRC-50 (NH$_4$+). The fractions containing the object compound were concentrated to about 20 ml under reduced pressure. The resultant solution was adjusted to pH 6 with 1N hydrochloric acid and lyophilized to give 4-N-oleoyl-5-de-O-methylsporaricin B trihydrochloride (120 mg).

$[\alpha]_D^{20}$; +79.3° (C 0.5, H$_2$O).
IR (Nujol); 1600, 1500, 1400 cm$^{-1}$.
NMR (D$_2$O, δ); 3.20 (3H, s), 5.24–5.80 (3H, m).

EXAMPLE 12

(1) The following compound was obtained according to a similar manner to Example 1 (1).

1,2',6'-Tris-N-benzyloxycarbonyl-4-N-[(3RS)-3-hexadecanoyloxyoctadecanoyl]-5-de-O-methylsporaricin B.

$[\alpha]_D^{20}$; +50.1° (C 0.5, CHCl$_3$).
IR (Nujol); 1690, 1620, 1510, 1245, 1230 cm$^{-1}$.
NMR (CDCl$_3$, δ); 3.05 (3H, s), 5.10 (6H, s).
FD Mass; 1242 (M+ +1).

(2) The following compound was obtained according to a similar manner to Example 1 (2).

4-N-[(3RS)-3-Hexadecanoyloxyoctadecanoyl]-5-de-O-methylsporaricin B.

mp; 222°–224° C. (dec.).
$[\alpha]_D^{20}$; +53.4° (C 1.0, CH$_3$OH).
IR (Nujol); 1730, 1600, 1490, 1170, 1110 cm$^{-1}$.
FD Mass; 840 (M+ +1).

EXAMPLE 13

(1) The following compound was obtained according to a similar manner to that of Example 1 (1).

1,2',6'-Tris-N-benzyloxycarbonyl-4-N-(10-undecenoyl)-5-de-O-methylsporaricin B.

IR (Nujol); 3280, 1710–1680, 1610, 1510, 1240, 1030, 1010 cm$^{-1}$.
NMR (CDCl$_3$, δ); 3.03 (3H, s).

(2) Ozone was blowed into a solution of 1,2',6'-tris-N-benzyloxycarbonyl-4-N-(10-undecenoyl)-5-de-O-methylsporaricin B (6.711 g) in a mixture of dichloromethane (60 ml) and methanol (15 ml) at −65° C. until the solution was coloured to blue. Dry nitrogen was blowed into the mixture at the same temperature for 3 minutes. Sodium borohydride (1.52 g) was added to the mixture at −65° C. and the mixture was warmed up to ambient temperature. The mixture was stirred at ambient temperature for 30 minutes. The mixture was washed with saturated aqueous sodium chloride, dried over sodium sulfate, and concentrated in vacuo. The residue was purified by a column chromatography on silica gel (140 g) [chloroform-methanol 50:1 (V/V)].

The fractions which were contained the desired material were concentrated in vacuo to give 1,2',6'-tris-N-benzyloxycarbonyl-4-N-(10-hydroxyundecanoyl)-5-de-O-methylsporaricin B (5.86 g) as a glass.

IR (Nujol); 1720–1680, 1620–1590, 1510 cm$^{-1}$.
NMR (CDCl$_3$, δ); 3.03 (3H, s).

(3) The following compound was obtained according to a similar manner to that of Example 1 (2).

mp; 216° C. (dec.).
$[\alpha]_D^{23}$; +84.3° (C 20.5, H$_2$O).
IR (Nujol); 1600 cm$^{-1}$.
NMR (D$_2$O, δ); 3.10 (3H, s), 5.43 (1H, d, J=3 Hz).
FD Mass; 489 (M+).

EXAMPLE 14

(1) To a solution of 1,2',6'-tris-N-benzyloxycarbonyl-4-N-(10-hydroxydecanoyl)-5-de-O-methylsporaricin B (4 g) in pyridine (40 ml) was added p-toluenesulfonyl chloride (1.29 g) at −40° C. The mixture was stirred at −40° C. for 3 hours and at −20° C. for 1 hour. Additional amount of p-toluenesulfonyl chloride (460 mg) was added to the mixture at −20° C. and the mixture was stirred at the same temperature for 1 hour. The mixture was stirred at −10° C. for 2 hours and at 0° C. for 2 hours, and the mixture was stood in ice-box (5° C.) for 2 days. Ice-water was added to the mixture. The mixture was concentrated in vacuo. The residue was dissolved in ethyl acetate. The mixture was washed with saturated aqueous sodium chloride, dried over magnesium sulfate, and concentrated in vacuo. The residue was purified by a column chromatography on silica gel (150 g) [chloroform-methanol 50:1 (V/V)]. The fraction, which were contained the desired material, were concentrated in vacuo to give 1,2',6'-tris-N-benzyloxycarbonyl-4-N-[10-(p-toluenesulfonyloxy)-decanoyl]-5-de-O-methylsporaricin B (2.09 g).

IR (Nujol); 1710 (sh), 1700 (sh), 1680 cm$^{-1}$.
NMR (CDCl$_3$, δ); 2.43 (3H, s), 3.00 (3H, s), 7.80 (2H, d, J=8 Hz).

(2) A mixture of 1,2',6'-tris-N-benzyloxycarbonyl-4-N-[10-(p-toluenesulfonyloxy)decanoyl]-5-de-O-methylsporaricin B (500 mg), sodium azide (155 mg), and ammonium chloride (128 mg) in N,N-dimethylformamide (10 ml) was stirred at 100° C. for 2 hours under argon atmosphere. The mixture was poured into ice water (100 ml). The resulted mixture was extracted with ethyl acetate three times. The extract was washed with water three times, dried over sodium sulfate, and concentrated in vacuo. The residue was purified by a column chromatography on silica gel (15 g) [chloroform-methanol 50:1 (V/V)]. The fractions, which was contained the desired material, were concentrated in vacuo to give 4-N-(10-azido-decanoyl)-1,2',6'-tris-N-benzyloxycarbonyl-5-de-O-methylsporaricin B (359 mg).

IR (Nujol); 2090, 1680, 1610, 1500 cm$^{-1}$.
NMR (CDCl$_3$, δ); 3.00 (3H, s).

(3) A solution of 4-N-(10-azidodecanoyl)-1,2',6'-tris-N-benzyloxycarbonyl-5-de-O-methylsporaricin B (342 mg) in a mixture of methanol (10 ml) and conc. hydrochloric acid (0.2 ml) was hydrogenated under 3.5 atmospheric pressure of hydrogen at ambient temperature for 5 hours in the presence of palladium black (180 mg). The catalyst was filtered off. The filtrate was concentrated in vacuo. The residue was dissolved in aqueous ethanol. The solution was concentrated in vacuo. This procedure was twice repeated. The residue was dissolved in water (10 ml) and the aqueous solution was lyophilized to give 4-N-(10-aminodecanoyl)-5-de-O-methylsporaricin B tetrahydrochloride (239 mg).

mp; 225° C. (dec.).
$[α]_D^{23}$; +85.9° (C=0.5, H$_2$O).
IR (Nujol); 1590 cm$^{-1}$.
NMR (D$_2$O, δ); 3.17 (3H, s), 5.53 (1H, d, J=3 Hz).
FD Mass; 487 (M+ −1).

EXAMPLE 15

(1) A solution of 1,2',6'-tris-N-benzyloxycarbonyl-4-N-(10-undecenoyl)-5de-O-methylsporaricin B (3 g) and m-chloroperbenzoic acid (2.19 g) in dichloromethane (50 ml) was refluxed for 5 hours. The reaction mixture was concentrated under reduced pressure. The residue was dissolved in ethyl acetate. The organic solution was washed with saturated aqueous sodium hydrogen carbonate, aqueous potassium carbonate, and water in turn, dried over sodium sulfate, and concentrated under reduced pressure to give 1,2',6'-tris-N-benzyloxycarbonyl-4-N-[(10RS)-10,11-epoxyundecanoyl]-5-de-O-methylsporaricin B (2.72 g).

IR (Nujol); 3280, 1710–1690, 1610 cm$^{-1}$.
NMR (CDCl$_3$, δ); 3.03 (3H, s).

(2) A mixture of 1,2',6'-tris-N-benzyloxycarbonyl-4-N-[(10RS)-10,11-epoxyundecanoyl]-5-de-O-methylsporaricin B (1 g), sodium azide (216 mg), and ammonium chloride (178 mg) in N,N-dimethylformamide (10 ml) was stirred at 100° C. for 4 hours. To the mixture was added the mixture of sodium azide (216 mg), ammonium chloride (178 mg), and N,N-dimethylformamide (10 ml). The mixture was stirred at 100° C. for additional 4 hours. The mixture was poured into ice-water. The resultant mixture was extracted with ethyl acetate. The ethyl acetate layer was washed with water, dried over sodium sulfate, and concentrated under reduced pressure. The residue (1 g) was subjected to a column chromatography on silica gel (30 g) and eluted with a mixture of chloroform and methanol (100:1 V/V) and chloroform and methanol (10:1 V/V) in turn. The fractions containing the object compound were combined and concentrated under reduced pressure to give 4-N-[(10RS)1-11-azide-10-hydroxyundecanoyl]-1,2',6'-tris-N-benzyloxycarbony-5-de-O-methylsporaricin B (859 mg).

IR (Nujol); 2100, 1710–1680, 1610, 1510, 1240 cm$^{-1}$.
NMR (CDCl$_3$, δ); 3.04 (3H, s).

(3) The following compound was obtained according to a similar manner to that of Example 14 (3).

4-N-[(10RS)-11-Amino-10-hydroxyundecanoyl]-5-de-O-methylsporaricin B tetrahydrochloride.
mp; 218° C. (dec.).
$[α]_D^{22}$; +76.9° (C=1.0 H$_2$O).
IR (Nujol); 1600 cm$^{-1}$.
NMR (D$_2$O, δ); 3.17 (3H, s), 5.53 (1H, d, J=3 Hz).
FD Mass; 518 (M+).

EXAMPLE 16

(1) Trifluoroacetic acid (10 ml) was added to 1,2',6'-tris-N-benzyloxycarbonyl-4-N-[(10RS)-10,11-epoxyundecanoyl]-5-de-O-methylsporaricin B (1 g) under ice-cooling. The mixture was stirred at the same temperature for 5 hours and at ambient temperature for 1 hour. The mixture was concentrated under reduced pressure. The residue was dissolved in toluene. The solution was concentrated under reduced pressure. The residue was dissolved in ethyl acetate. The organic solution was washed with 10% aqueous potassium carbonate and aqueous sodium hydrogen carbonate, dried over sodium sulfate, and concentrated under reduced pressure. To the residue was added a solution of potassium hydroxide (124 mg) in methanol (20 ml) at ambient temperature. The solution was stirred at the same temperature for 30 minutes. Acetic acid (0.2 ml) was added to the reaction mixture at ambient temperature. The mixture was concentrated in vacuo. The residue was dissolved in ethyl acetate. The organic solution was washed with water, dried over sodium sulfate, and concentrated in vacuo. The residue (1 g) was subjected to a column chromatography on silica gel (30 g) and eluted with chloroform-methanol [25:1 (V/V)]. The fractions containing the object compound were combined and concentrated in vacuo to give 1,2',6'-tris-N-benzyloxycarbonyl-4-N-[(10RS)-10,11-dihydroxyundecanoyl]-5-de-O-methylsporaricin B (447 mg).

IR (Nujol); 3280, 1720–1680, 1610, 1510, 1240, 1040, 1010 cm$^{-1}$.

(2) The following compound was obtained according to a similar manner to that of Example 1 (2)

4-N-[(10RS)-10,11-dihydroxyundecanoyl]-5-de-O-methylsporaricin B.
mp; 198° C. (dec.).
$[α]_D^{22}$; +70.6° (C=1.0 H$_2$O).
IR (Nujol); 1600, 1500 cm$^{-1}$.
NMR (D$_2$O, δ); 3.16 (3H, s), 5.48 (1H, d, J=4 Hz).
FD Mass; 519 (M+).

EXAMPLE 17

(1) To a solution of sporaricin B (2.19 g) in methanol (60 ml) was added nickel acetate tetrahydrate (3.28 g) and the solution was stirred at ambient temperature for an hour. N-(Benzyloxycarbonyloxy)succinimide (5.30 g), was added to the solution and the mixture was stirred at ambient temperature for an hour. Conc. aqueous ammonia was added to the mixture. The solution was stirred at the same temperature for half an hour and concentrated under reduced pressure to give a syrup. A solution of the syrup in chloroform (200 ml) was washed with 3N aqueous ammonia (200 ml), 4% aqueous sodium hydrogen carbonate (200 ml), and water (200 ml), in turn, dried over magnesium sulfate, and concentrated under reduced pressure to give a syrup. The syrup was subjected to a column chromatography on silica gel (100 g), and eluted with methanol-chloroform [1:99 and 2:98 (V/V), in turn] to give two fractions (first Fraction A and second Fraction B). From the first Fraction A, a by-product, 1,4,2',6'-tetrakis-N-benzyloxycarbonylsporaricin B was given as a glass, (0.79 g).
mp; 72°–76° C.
$[α]_D^{24}$; +40° (C 1.0, CHCl$_3$).

IR (Nujol); 1730–1680 cm$^{-1}$.
NMR (CDCl$_3$, δ); 1.06 (3H, d, J=6 Hz), 2.94 (3H, s), 3.31 (3H, s).
FD Mass; 869 (M+).

Further, from the second Fraction B, the desired product, 1,2',6'-tris-N-benzyloxycarbonylsporaricin B was given as a glass (4.23 g).
mp; 56°–62° C.
[α]$_D^{24}$; +62.5° (C 1.0, CHCl$_3$).
IR (Nujol); 3300, 1720–1680 cm$^{-1}$.
NMR (CDCl$_3$ δ); 1.08 (3H, d, J=7 Hz), 2.22 (3H, br. s), 3.37 (3H, s).
FD Mass; 735 (M+).

(2) The following compound was obtained according to a similar manner to that of Example 1 (1).
1,2',6'-Tris-N-benzyloxycarbonyl-4-N-palmitoyl-sporaricin B.
NMR (CDCl$_3$, δ); 2.97 (3H, s), 3.30 (3H, s).

(3) The following compound was obtained according to a simlar manner to that of Example 1 (2).
4-N-Palmitoylsporaricin B trihydrochloride.
mp; 237° (dec.).
IR (Nujol); 1600 cm$^{-1}$.
NMR (D$_2$O, δ); 3.10 (3H, s), 3.40 (3H, s), 5.50 (1H, d, J=3 Hz).
FD MAss; 571 (M+).

EXAMPLE 18

(1) To a solution of 1,2',6'-tris-N-benzyloxycarbonyl-fortimicin B (517 mg) in a mixture of tetrahydrofuran (20 ml) and water (5 ml) was added palmitoyl chloride (208 mg) under ice-cooling, keeping the pH between 8 and 9 with triethylamine. The mixture was stirred for 30 minutes under the same condition. The mixture was concentrated in vacuo. The residue dissolved in ethyl acetate was washed with water and saturated aqueous sodium chloride in turn, dried over magnesium sulfate, and concentrated in vacuo. The residue was purified by a column chromatography on silica gel (20 g) [eluted; chloroform and methanol 100:1 (V/V)]. The fraction containing the desired compound were combined and concentrated in vacuo to give 1,2',6'-tris-N-benzyloxycarbonyl-4-N-palmitoylfortimicin B (477 mg).
IR (CHCl$_3$); 1700, 1500 cm$^{-1}$.
NMR (CDCl$_3$, δ); 2.87 (3H, s), 3.33 (3H, s).

(2) A solution of 1,2',6'-tris-N-benzyloxycarbonyl-4-N-palmitoylfortimicin B (446 mg) in a mixture of methanol (13 ml) and 1N hydrochloric acid (2 ml) was hydrogenated under 1 atmosphere pressure of hydrogen in the presence of palladium black (380 mg) at ambient temperature for 5 hours. The catalyst was removed by and washed with water. The filtrate and washings were combined and lyophilized to give 4-N-palmitoylfortimicin B trihydrochloride (312 mg).
mp; 208° C. (dec.).
[α]$_D^{26}$; +71.0° (C=0.49, H$_2$O).
IR (Nujol); 1600 cm$^{-1}$.
NMR (CD$_3$OD, δ); 3.17 (3H, s), 3.47 (3H, s), 5.33 (1H, d, J=3 Hz).
FD Mass; 587 (M+).

EXAMPLE 19

4-N-Palmitoyl-5-de-O-methylsporaricin B trihydrochloride: 1%
Polyethyleneglycol: 2.6%
Mineral oil: 8%
White bees wax: 9%
White petrolatum: 79.4%

The above ingredients are blended and kneaded into ointment.

EXAMPLE 20

(1) A solution of 1,2',6'-tris-N-benzyloxycarbonyl-5-de-O-methylsporaricin B (7.20 g) and pentadecanyl isocyanate (4.85 g) in tetrahydrofuran (50 ml) was stirred at ambient temperature for 5 hours. Conc. aqueous ammonia (5 ml) was added to the reaction mixture and the solution was stirred at the ambient temperature for one hour. The solution was concentrated under reduced pressure to give a syrup. The syrup was subjected to a column chromatography on silica gel (100 g) and eluted with methanol-chloroform (5:95 V/V). The fractions containing the object compound were collected and concentrated under reduced pressure to give 1,2',6'-tris-N-benzyloxycarbonyl-4-N-pentadecanylcarbamoyl-5-de-O-methylsporaricin B as a solid (9.70 g).
mp; 107°–108° C.
IR (Nujol); 1720–1680 cm$^{-1}$.
NMR (DMSO-d$_6$-TMS, δ); 2.88 (3H, s).

(2) A solution of 1,2',6'-tris-N-benzyloxycarbonyl-4-N-pentadecanylcarbamoyl-5-de-O-methylsporaricin B (500 mg) in a mixture of ethyl acetate (10 ml) and 1N hydrochloric acid (10 ml) was hydrogenated under one atmospheric pressure of hydrogen at ambient temperature for 6 hours in the presence of 10% palladium on carbon (300 mg). The catalyst was filtered off. The aqueous layer was washed with hexane and lyophilized to give 4-N-pentadecanylcarbamoyl-5-de-O-methylsporaricin B trihydrochloride as a solid (145 mg).
mp; 230° C. (dec.).
[α]$_D^{20}$; +62.9° (C 1.0, H$_2$O).
IR (KBr); 1600 cm$^{-1}$.
NMR (D$_2$O-TSP, δ); 2.95 (3H, s).
FDMS; 572 (M+).

We claim:
1. A compound of the formula:

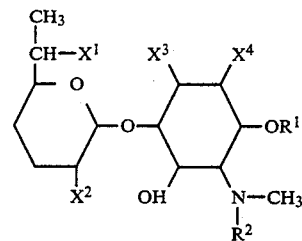

wherein $X^1$, $X^2$ and $X^3$ are each amino or protected amino,
$X^4$ is hydrogen or hydroxy,
$R^1$ is hydrogen or lower alkyl, and
$R^2$ is higher $C_{10-24}$ alkanoyl or said alkanoyl substituted with hydroxy, amino, azido, epoxy, protected hydroxy or protected amino, higher $C_{10-24}$ alkenoyl, or higher $C_{10-24}$ alkylcarbamoyl, or pharmaceutically acceptable salt thereof.

2. A compound according to claim 1, in which
$X^4$ and $R^1$ are each as defined in claim 1,
$X^1$, $X^2$ and $X^3$ are each amino,
$R^2$ is higher alkanoyl or said alkanoyl substituted with hydroxy or protected hydroxy, higher alkenoyl, or higher alkylcarbamoyl.

3. A compound according to claim 2, which is a sporaricin B derivative of the formula:

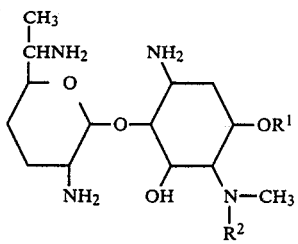

wherein R¹ and R² are each defined in claim 2, or pharmaceutically acceptable salt thereof.

4. A compound according to claim 3, in which
R¹ is hydrogen and
R² is higher alkanoyl.

5. A compound according to claim 4, which is 4-N-palmitoyl-5-de-O-methylsporaricin B or pharmaceutically acceptable salt thereof.

6. A compound according to claim 4, which is 4-N-decanoyl-5-de-O-methylsporaricin B or pharmaceutically acceptable salt thereof.

7. A compound according to claim 4, which is 4-N-lauroyl-5-de-O-methylsporaricin B or pharmaceutically acceptable salt thereof.

8. A compound according to claim 4, which is 4-N-myristoyl-5-de-O-methylsporaricin B or pharmaceutically acceptable salt thereof.

9. A compound according to claim 4, which is 4-N-stearoyl-5-de-O-methylsporaricin B or pharmaceutically acceptable salt thereof.

10. A compound according to claim 4, which is 4-N-eicosanoyl-5-de-O-methylsporaricin B or pharmaceutically acceptable salt thereof.

11. A compound according to claim 4, which is 4-N-docosanoyl-5-de-O-methylsporaricin B or pharmaceutically acceptable salt thereof.

12. A compound according to claim 3, which is 4-N-(3-hydroxytetradecanoyl)-5-de-O-methylsporaricin B or pharmaceutically acceptable salt thereof.

13. A compound according to claim 3, which is 4-N-(3-hexadecanoyloxyoctadecanoyl)-5-de-O-methylsporaricin B or pharmaceutically acceptable salt thereof.

14. A compound according to claim 3, which is 4-N-oleoyl-5-de-O-methylsporaricin B or pharmaceutically acceptable salt thereof.

15. A compound according to claim 3, which is 4-N-palmitoylsporaricin B or pharmaceutically acceptable salt thereof.

16. A compound according to claim 2, which is a fortimicin B derivative of the formula:

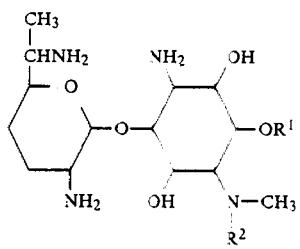

wherein R¹ and R² are each as defined in claim 2, or pharmaceutically acceptable salt thereof.

17. A compound according to claim 16, which is 4-N-palmitoylfortimicin B or pharmaceutically acceptable salt thereof.

18. A pharmaceutical antimicrobial composition comprising, as an active ingredient, the compound of claim 1, in association with a non-toxic, pharmaceutically acceptable carrier or excipient.

* * * * *